(12) United States Patent
Matsuda et al.

(10) Patent No.: US 8,575,175 B2
(45) Date of Patent: Nov. 5, 2013

(54) THERAPEUTIC AGENT FOR CHRONIC RENAL FAILURE

(75) Inventors: Fuko Matsuda, Kamakura (JP);
Katsuhiko Iseki, Kamakura (JP);
Hajimu Kurumatani, Kamakura (JP);
Mitsuko Miyamoto, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 193 days.

(21) Appl. No.: 13/055,242

(22) PCT Filed: Jul. 23, 2009

(86) PCT No.: PCT/JP2009/063153
§ 371 (c)(1),
(2), (4) Date: Mar. 30, 2011

(87) PCT Pub. No.: WO2010/010909
PCT Pub. Date: Jan. 28, 2010

(65) Prior Publication Data
US 2011/0178103 A1    Jul. 21, 2011

(30) Foreign Application Priority Data
Jul. 23, 2008    (JP) .................................. 2008-190085

(51) Int. Cl.
*A61K 31/4965* (2006.01)

(52) U.S. Cl.
USPC .................................................. 514/255.06

(58) Field of Classification Search
USPC ....................................... 514/255.06; 544/336
See application file for complete search history.

(56) References Cited

U.S. PATENT DOCUMENTS 7,205,302 B2 * 4/2007 Asaki et al. ................ 514/252.1
2012/0101276 A1 4/2012 Itou et al.

FOREIGN PATENT DOCUMENTS

| EP | 1 013 639 A1 | 6/2000 |
|---|---|---|
| EP | 1106176 A1 | 6/2001 |
| EP | 1400518 A1 | 3/2004 |
| EP | 1913946 A1 | 4/2008 |
| WO | WO 97/03973 A1 | 2/1997 |
| WO | 99/21843 A1 | 5/1999 |
| WO | 99/32435 A1 | 7/1999 |
| WO | 01/16132 A1 | 3/2001 |
| WO | WO 2005/067927 A2 | 7/2005 |
| WO | WO 2010/075861 A2 | 7/2010 |
| WO | WO 2010/150865 A1 | 12/2010 |

OTHER PUBLICATIONS

Asaki et al. CAS: 137: 370112, 2002.*
Extended European Search Report, dated Apr. 18, 2012, for Application No. 09800423.7.
International Preliminary Report on Patentability and translation of Written Opinion of the International Searching Authority, dated Mar. 8, 2011, for International Application No. PCT/JP2009/063153.
Takenaka et al., "Neko no Mansei Jinfuzen ni Taisuru Beraprost Natrium no Chiryo Koka ni Tsuite no Kento", Annual Meeting of Japanese Society of Clinical Veterinary Medicine Puroshidingu, vol. 26., No. 3., 2005, pp. 72-76.

* cited by examiner

*Primary Examiner* — Rei-tsang Shiao
(74) *Attorney, Agent, or Firm* — Birch, Stewart, Kolasch & Birch, LLP

(57) ABSTRACT

The present invention aims to provide a therapeutic agent for chronic renal failure, comprising as an effective ingredient a compound represented by General Formula (1) or a pharmaceutically acceptable salt thereof. That is, the present invention provides provision of a drug comprising as an effective ingredient a compound represented by General Formula (1) or a pharmaceutically acceptable salt thereof, which drug is useful not only for amelioration of renal function, but also for amelioration of anemia, activation of SOD and excretion of uremic substances.

6 Claims, 2 Drawing Sheets

Each value represents mean±standard error calculated from 7 cases in each group or 4 cases in the normal group.

Each value represents mean±standard error calculated from 7 cases in each group or 4 cases in the normal group.

Each value represents mean±standard error calculated from 7 cases in each group or 4 cases in the normal group.

Each value represents mean±standard error calculated from 3 cases in each group.

THERAPEUTIC AGENT FOR CHRONIC RENAL FAILURE

TECHNICAL FIELD

The present invention relates to a therapeutic agent for chronic renal failure which has a non-prostanoid skeleton and contains a $PGI_2$-receptor agonist as an effective ingredient.

BACKGROUND ART

Recently, the number of patients who need dialysis because of a decrease in renal function tends to increase year by year. The reasons therefor include changes in the living environment, aging and the increase in the number of patients suffering from diabetic nephropathy due to the increase in the number of patients suffering from diabetes mellitus in recent years.

Renal failure is the state wherein excretion of nitrogen metabolites, water and/or electrolytes is insufficient due to blood flow obstruction in kidney, decreased functional nephron and/or obstruction of the urinary tract, leading to incapability to maintain quantitative and qualitative homeostasis of the body fluid. Renal failure includes acute renal failure and chronic renal failure, and both of these show increases in blood urea nitrogen (BUN) and serum creatinine. However, since they show large differences in the speed of progress of the diseased state and in reversibility of the decrease in renal function, they are evidently different diseases. Acute renal failure suddenly occurs and progresses daily (with an increase in the serum creatinine level by not less than 0.5 mg/dL per day as a criterion), but, by removal of its cause, sufficient whole-body control and appropriate conservative treatment or dialysis treatment, recovery of renal function can be basically expected (Non-patent Document 1). On the other hand, establishment of chronic renal failure requires a long period of time. That is, when a renal disease which may cause glomerulonephritis or diabetic nephropathy has gradually progressed year by year resulting in evident increases in BUN and the serum creatinine level, the patient is diagnosed with chronic renal failure. At this time point when the increase in the serum creatinine level is observed, the filtering function for low-molecular waste products, which is the most important function of the kidney, is remarkably decreased; the glomerular filtration rate is not more than 50%; and the decrease in renal function is irreversible. After the establishment of chronic renal failure, renal function gradually decreases for several years, and, when the glomerular filtration rate has decreased to not more than 10%, the chronic renal failure is in the terminal stage, and dialysis or renal transplantation is necessary. Therefore, in therapy of chronic renal failure in the conservative stage, it is important to delay the timing of the transition to dialysis as much as possible (Non-patent Documents 2 and 3).

Examples of the causative diseases of chronic renal failure include nephropathic diseases such as primary renal diseases; renal disorders due to systemic diseases; congenital renal diseases; renal infections; renal disorders due to nephrotoxic substances; and obstructive diseases of the urinary tract. Among these, examples of the major causative diseases include chronic glomerulonephritis, diabetic nephropathy, chronic pyelonephritis, nephrosclerosis and cystic kidney. Especially, the ratios of chronic glomerulonephritis, diabetic nephropathy and nephrosclerosis are high, and, because of the drastic increase in the number of patients suffering from diabetes mellitus in recent years, the ratio of chronic renal failure whose causative disease is diabetic nephropathy has significantly increased.

In chronic renal failure, clinical symptoms such as pulmonary congestion and congestive heart failure due to decreased urine output; neurological and psychotic symptoms due to progress of uremia; anemia due to a decrease in erythropoietin produced in the kidney; and electrolyte imbalances such as hyponatremia and hyperkalemia; as well as digestive symptoms, abnormal bone metabolism and abnormal sugar metabolism, are commonly observed independently of the causative disease of the chronic renal failure.

Further, it is said that chronic renal failure has a common mechanism of progression which is independent of its primary disease. For example, in a commonly used textbook of internal medicine, there is the following description: "In general, in chronic renal failure, progression of chronic renal failure is observed even during a period when the primary disease is suppressed, so that a common mechanism of the decrease in renal function other than the cause of each renal disease is considered to exist." (Non-patent Document 4).

Further, chronic renal failure is known to show common clinical symptoms even in cases where the causative underlying disease is different. That is, it is said that "Irrespective of whether the disease is primary or secondary, most renal diseases with a chronic process result in an irreversible decrease in renal function after progression of the diseased state, and then become to be called chronic renal failure. This diseased state finally leads to a type of syndrome called uremia, in which the difference depending on the type of the underlying disease is hardly observed and common clinical symptoms appear." (Non-patent Document 5).

Further, it is said that, in the pathological findings of the kidney, "kidneys of patients suffering from end-stage chronic renal failure show common tissue images in most cases even in cases where the patients have different underlying diseases, and therefore pathological diagnosis of the underlying diseases are often difficult." (Non-patent Document 6).

Thus, although there are various possible causative diseases of chronic renal failure, it is a characteristic disease distinguishable from the other renal diseases, since it shows characteristic clinical symptoms different from the other renal diseases; it has a common mechanism of progression of the diseased state which is different from that of the primary disease; it shows characteristic findings which do not reflect its causative disease in the pathological findings; and its therapy requires a therapeutic method specific to chronic renal failure.

During the conservative stage before beginning dialysis, therapy of chronic renal failure is based on diet therapies including low protein diets and high-calorie diets, and also includes restriction of salt and water as well as usage of an antihypertensive drug for management of hypertension, which is a risk factor for exacerbation of chronic renal failure. Further, to slow down progression of the diseased state or to ameliorate uremia, oral activated carbon adsorbent preparations may be used in some cases. However, in spite of these therapies, progression of renal failure cannot be well prevented at present, and the number of patients who require hemodialysis because of onset of uremic symptoms due to progression of renal function disorder is consistently increasing. The survival rate of chronic renal failure patients who began dialysis has been improved by virtue of the recent progress in hemodialysis therapy, but there still remain many problems including not only the requirement of 2 to 3 times per week of hospital visit, but also onset of complications of long-term dialysis, infections, increased risks of onset of cardiovascular disturbances, high medical cost and the like. Especially in cases where the patient began dialysis because of diabetic nephropathy, the five-year survival rate is as small as not more than 50% (Non-patent Document 7).

As mentioned above, in chronic renal failure patients, various complications characteristic to chronic renal failure occur. Among these, anemia, which develops and is exacerbated as renal function decreases, is especially problematic. Anemia begins to develop when blood urea nitrogen (BUN) and blood creatinine begin to increase, and almost all the cases of dialysis patients and the like in end-stage renal failure, which then causes hypobulia, easy fatigability, breathlessness, postural vertigo and the like, leading to remarkable decreases in QOL of the patients.

Previously, transfusion was carried out for therapy of anemia due to chronic renal failure, but therapy with a recombinant erythropoietin preparation (rHuEPO preparation) has now become commonly carried out. However, problems such as the fact that therapy with this preparation needs hospital visit and accompanies pain because it is administered subcutaneously, and existence of drug-resistant patients due to occurrence of autoantibody have been pointed out for this therapy. Therefore, a prophylactic or therapeutic agent for anemia due to chronic renal failure, which can be easily administered, whose dosing management can be carried out at home, and whose side effects are small, is demanded.

In recent years, significant involvement of active oxygen in progression of chronic renal failure and exacerbation of complications of chronic renal failure has been pointed out. Superoxide dismutase (this may be hereinafter abbreviated as SOD) is widely distributed in the living bodies of animals, plants, microorganisms and the like, and especially important among the enzymes which decompose superoxide anion radicals (this may be hereinafter abbreviated as $O_2^-$) which are highly-reactive active oxygen. In chronic renal failure, the SOD activity contained in the kidney or liver decreases, and the decrease is strongly involved in decreased renal function and onset and exacerbation of complications of chronic renal failure such as cardiovascular disturbances, which are caused by active oxygen (Non-patent Document 8).

In chronic renal failure, low-molecular substances (uremic substances) which accumulate in the living body as renal function decreases cause development of clinical symptoms characteristic to chronic renal failure, which leads to exacerbation of cardiovascular disturbances and a further decrease in renal function. Indoxyl sulphate is a low-molecular substance produced by the process wherein indole produced in the intestine from tryptophan is absorbed into the living body, followed by being metabolized in the liver. Since indoxyl sulphate is excreted mainly from the kidney, efficient excretion is impossible in chronic renal failure because of the decrease in renal function, so that the blood level of indoxyl sulphate increases. Recent interest has focused on indoxyl sulphate as one of the causative substances responsible for exacerbation of various complications of chronic renal failure and exacerbation of cardiovascular disturbances due to endothelial dysfunction (Non-patent Document 9). It is also known that indoxyl sulphate itself is involved in exacerbation of renal disorders (Non-patent Document 10).

Indoxyl sulphate is actively excreted via OAT-3, which is an organic anion transporter existing mainly in the renal tubules, and it is known that OAT-3 decreases in chronic renal failure (Non-patent Document 11).

Further, it is known that the blood levels of various drugs, especially those of the renal excretion type, more easily increase in chronic renal failure compared to healthy individuals. Therefore, in many cases, in chronic renal failure patients, occurrence of side effects of drugs is more frequent and determination of appropriate doses of drugs is difficult. Decreases in drug transporters in the kidney are involved in such phenomena as one of the mechanisms thereof.

Thus, in treatment of chronic renal failure patients, it is important not only to suppress the decrease in the renal function to filtrate low-molecular substances, but also to suppress anemia and the increase in active oxygen caused as complications of the chronic renal failure as much as possible, as well as to prevent the decrease in the transporters which occurs with the renal disorder as much as possible.

Prostaglandin (PG) is a group of naturally-occurring compounds which show various physiological activities, and has the prostanoic acid skeleton in common. The naturally-occurring PGs are grouped, based on the structural features of their five-membered rings, into the PGAs, PGBs, PGCs, PGDs, PGEs, PGFs, PGGs, PGHs, PGIs and PGJs, and further grouped into subclasses such as 1, 2 and 3 based on the existence of unsaturation and/or oxidation. Further, their many synthetic analogues are known. $PGI_2$, which is typical among the PGI derivatives, is also called prostacyclin, and known to be a substance having a strong platelet aggregation inhibition action and peripheral vasodilator action.

It is already known that $PGI_2$ and several compounds among the derivatives thereof are effective for disease model animals for glomerulonephritis and diabetic nephropathy, and are clinically effective. However, such findings on $PGI_2$ and derivatives thereof are intended for primary diseases without onset of chronic renal failure. At this stage, renal disorder is evaluated with the urine protein and/or the urinary microalbumin, which increase as the barrier function of the glomerular basement membrane in the kidney to macromolecules is deteriorated. The pharmacological effects are also evaluated based on the decreases in these parameters.

Further, effectiveness of $PGI_2$ derivatives in chronic renal failure has also been reported (Patent Documents 1 to 10, Non-patent Documents 12 to 15). For example, results with m-phenylene $PGI_2$ derivatives including beraprost sodium have been reported, which results were obtained using a model rat subjected to partial nephrectomy and a model rat suffering from chronic renal failure which was prepared by administration of an anti-basement membrane antibody and whose primary disease was nephritis (Patent Document 1 and Non-patent Document 12). For accurate evaluation of renal function in chronic renal failure, glomerular filtration rate (GFR), which is a marker of the renal function to filtrate low-molecular substances, or, as an alternative, eGFR (estimated GFR: estimated glomerular filtration rate) or creatinine clearance is used, and, in addition, the serum creatinine level or BUN, which increases as the renal function to filtrate low-molecular substances decreases, is used. Also in Patent Document 1 and Non-patent Document 12, the serum creatinine level and BUN are used as indices for evaluation of the pharmacological effects. That is, in these rat models, occurrence of chronic renal failure defined with a serum creatinine level and BUN higher than their normal levels was confirmed, followed by beginning administration of a compound of an m-phenylene $PGI_2$ derivative. Thereafter, it was shown that increases of the markers for chronic renal failure, that is, the serum creatinine level and the BUN value, were suppressed compared to those in the control group.

In Patent Document 13, it is described that a $PGI_2$ derivative cicaprost ameliorated microalbuminuria in a canine mild chronic renal failure model, but this evaluation was carried out using the model wherein GFR was maintained at a level of 82% with respect to the normal level, so that the model had not developed chronic renal failure, with which GFR is expected to be not more than 50%. Further, the effect found was merely a decrease in microalbuminuria, which is a reversible change, rather than amelioration of the renal function to filtrate low-molecular substances.

It has been reported that, in chronic renal failure patients, administration of beraprost sodium reduced the rate of decrease in renal function, which is indicated by decrease in the creatinine clearance or in the reciprocal of serum creatinine (Non-patent Literature 14). It is described that a $PGI_2$ derivative treprostinil ameliorated renal function in view of urine production in chronic renal failure patients, but the observation was carried out merely on diuresis, and whether or not chronic renal failure is ameliorated has not been shown (Patent Document 2).

It has been shown that hypoxemia may promote production of erythropoietin via an increased production of renal endogenous $PGE_2$ and $PGI_2$ (Non-patent Document 15). Although the kidney is under hypoxic condition in chronic renal failure and hence productions of endogenous $PGE_2$ and $PGI_2$, as well as erythropoietin, are considered to increase, severe anemia is problematic. The reason for this is not clear, but it is considered that, in renal failure, the ameliorating effect by the mechanism according to this literature may not function sufficiently.

In terms of the ameliorating effect on anemia by $PGI_2$ or a derivative thereof, results showing amelioration of anemia in long-term dialysis patients have been reported only for beraprost sodium (Non-patent Document 16). However, what this literature shows is amelioration of anemia in long-term dialysis patients wherein most kidney cells have lost their intrinsic functions. The amelioration of anemia in a chronic renal failure rat model in the present invention is amelioration of anemia in chronic renal failure in the conservative stage, wherein a part of the cellular functions in the kidney is maintained, so that the diseased state is different from that in the above literature. Thus, the extent of the effect of beraprost sodium in chronic renal failure in the conservative stage cannot be assumed from this literature, and there is no disclosure about this in the literature, so that no remarkable difference in the effect can be assumed among $PGI_2$ derivatives. Further, an ameliorating effect of beraprost sodium on uremia has been reported for chronic renal failure patients. Although anemia is described as one of the particular complications of uremia, there is no description on a particular ameliorating effect of administration of beraprost on anemia (Patent Document 3).

Further, administration of $PGI_2$ or a derivative thereof increases the erythrocytic SOD activity in gastric mucosa of rat and in human systemic sclerosis patients having Raynaud's symptoms (Non-patent Documents 17 and 18), but there is no suggestion at all on whether or not the administration increases the renal SOD activity and whether or not the effect is different among $PGI_2$ and derivatives thereof in chronic renal failure in which the target organ and the disease are totally different. Further, it has not been known that the administration suppresses decreases in renal organic anion transporters in renal failure.

All of cicaprost, m-phenylene $PGI_2$ derivatives, especially beraprost sodium, and further, treprostinil, which are compounds used in the above-mentioned literatures, are $PGI_2$ derivatives produced by improvement of instability of naturally occurring $PGI_2$.

On the other hand, in recent years, $PGI_2$-receptor agonists having a non-prostanoid skeleton have begun to be developed.

It has been pointed out that, among these, compounds represented by the General Formula below:

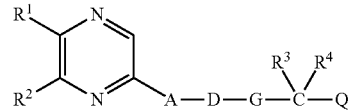

have the $PGI_2$-receptor agonistic activity and show the antiplatelet action, vasodilator action, bronchodilator action and the like, and that these may be useful for diseases such as transient cerebral ischemic attack, diabetic neuropathy, diabetic gangrene and peripheral circulatory disturbance. Further, in the Examples of this Patent Document, it has been confirmed that the compounds have the antiplatelet action which is an index for the $PGI_2$-receptor agonistic activity. It is described, in this Patent Document, that the compounds represented by the above General Formula are useful as therapeutic agents for glomerulonephritis and diabetic nephropathy, similarly to the other $PGI_2$-receptor agonists (Patent Document 4).

However, there is no description at all on characteristic and remarkable effectiveness of the compounds represented by the above General Formula as therapeutic agents for especially chronic renal failure among renal diseases.

Further, in Patent Documents 5 to 10, it is disclosed that $PGI_2$-receptor agonists having non-prostanoid skeletons can be used for renal failure, but there is no description at all on characteristic and remarkable effectiveness of the agonists as therapeutic agents for chronic renal failure.

That is, there is neither description nor suggestion on the fact that usage of the above compounds as therapeutic agents for chronic renal failure ameliorates the renal function to filtrate low-molecular substances; ameliorates anemia as a significant complication of chronic renal failure; and further, increases the activity of SOD which plays a central role in removal of active oxygen; and/or suppresses decrease in the organic anion transporters responsible for active excretion of uremic substances.

Prior Art References

Patent Documents

Patent Document 1: WO 2000/067748
Patent Document 2: WO 2005/058329
Patent Document 3: WO 2007/007668
Patent Document 4: WO 2002/088084
Patent Document 5: WO 1997/03973
Patent Document 6: WO 1999/21843
Patent Document 7: WO 1999/32435
Patent Document 8: WO 2001/016132
Patent Document 9: WO 2004/034965
Patent Document 10: JP 2000-191523 A Non-Patent Documents Non-patent Document 1: Kenjiro Kimura et al. eds., "Lecture Transcript: Renal Medicine, 1st Ed.", Medical View Co., Ltd., 2004, p. 270, ll. 1 to 10.

Non-patent Document 2: Kenjiro Kimura et al. eds., "Lecture Transcript: Renal Medicine, 1st Ed.", Medical View Co., Ltd., 2004, pp. 274-275.

Non-patent Document 3: Masaomi Nangaku, Folia Pharmacol Jpn, 118:68-70, 2001.

Non-patent Document 4: "Hyper Reference for Internal Medicine", Nakayama Shoten Co., Ltd., 1997.

Non-patent Document 5: Kiyoshi Kurokawa ed., "Nephrology—Approach from Pathophysiology", Nankodo Co., Ltd., 1995, p. 345, left column, ll. 1 to 7.

Non-patent Document 6: Kiyoshi Kurokawa ed., "Nephrology—Approach from Pathophysiology", Nankodo Co., Ltd., 1995, p. 347, left column, ll. 3 to 5.

Non-patent Document 7: Villar E, et al., J Am Soc Nephrol, 18: 2125-2134. 2007.

Non-patent Document 8: Vaziri N D, et al., Kidney Int, 63: 179-185. 2003.

Non-patent Document 9: Dou L, et al., Kidney Int, 65: 442-451. 2004.

Non-patent Document 10: Enomoto A, et al., Ther Apher Dial, 11 Supple 1: S27-31. 2007.

Non-patent Document 11: Villar S R, et al., Kidney Int, 68: 2704-2713. 2005.

Non-patent Document 12: Yamada M, et al., Eur J Pharmacol, 449: 167-176. 2002.

Non-patent Document 13: Villa E, et al., Am J Hypertens, 6: 253-257. 1993.

Non-patent Document 14: Fujita T, et al., Prostaglandins Leukot Essent Fatty Acids, 65: 223-227. 2001.

Non-patent Document 15: Kiyoshi Kurokawa ed., "Nephrology—Approach from Pathophysiology", Nankodo Co., Ltd., 1995, pp. 48-49.

Non-patent Document 16: Hidekazu Moriya, Abstract for Meeting of Japanese Society for Dialysis Therapy, O-425, 2006.

Non-patent Document 17: Zsoldos T, et al., Acta Physiol Hung, 64: 325-330. 1984.

Non-patent Document 18: Balbir-Gurman A, et al., Clin Rheumatol, 26: 1517-1521. 2007

DISCLOSURE OF THE INVENTION

Problems to be Solved by the Invention

Since, in a chronic renal failure patient, irreversible decrease in the renal function to filtrate low-molecular substances occurs, it is demanded to slow down the decrease to extend the period before introduction of dialysis as much as possible. Further, suppression of anemia as a complication which occurs with progression of chronic renal failure, and suppression of increase in oxidative stress as a cause of cardiovascular disturbances and vascular endothelial cell dysfunction need to be achieved as effectively as possible. Still further, amelioration of uremia caused by chronic renal failure and overcoming of increase in, and difficulty in control of, the blood levels of drugs observed in chronic renal failure need to be achieved. The present invention aims to provide a therapeutic agent for, and a method for treatment of, chronic renal failure to improve these problems.

Means for Solving the Problems

The above problems can be solved with a therapeutic agent for chronic renal failure containing as an effective ingredient a compound represented by General Formula (1) which is a $PGI_2$-receptor agonist, or a pharmaceutically acceptable salt thereof.

That is, the present invention is:

[1] a therapeutic agent for chronic renal failure containing as an effective ingredient: a compound represented by General Formula (1) below:

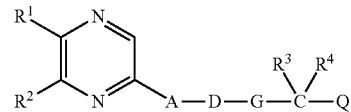

[wherein
$R^1$ and $R^2$ each independently represents aryl;
A represents $NR^5$, O, S, SO or $SO_2$;
$R^5$ represents $C_1$-$C_6$ alkyl, $C_2$-$C_6$ alkenyl or $C_3$-$C_6$ cycloalkyl;
D represents $C_2$-$C_6$ alkylene or alkenylene;
G represents O, S, SO or $SO_2$;
$R^3$ and $R^4$ each independently represents hydrogen or $C_1$-$C_6$ alkyl; and
Q represents carboxyl, $C_1$-$C_6$ alkoxycarbonyl, tetrazolyl or General Formula (2) below:

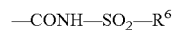

(wherein $R^6$ represents $C_1$-$C_6$ alkyl)]
or a pharmaceutically acceptable salt thereof;

[2] the therapeutic agent for chronic renal failure according to [1], wherein
$R^1$ and $R^2$ represent phenyl;
$R^5$ represents $C_1$-$C_6$ alkyl;
D represents $C_2$-$C_6$ alkylene;
G represents O;
$R^3$ and $R^4$ represent hydrogen; and
Q represents carboxyl or General Formula (2);

[3] the therapeutic agent for chronic renal failure according to [1] or [2], wherein
A represents $NR^5$;
$R^5$ represents $C_3$-$C_6$ branched alkyl;
D represents butylene; and
Q represents carboxyl or General Formula (2);

[4] the therapeutic agent for chronic renal failure according to any one of [1] to [3], wherein
$R^5$ represents isopropyl; and
Q represents carboxyl or General Formula (2);

[5] the therapeutic agent for chronic renal failure according to any one of [1] to [4], wherein
Q represents carboxyl;

[6] the therapeutic agent for chronic renal failure according to any one of [1] to [5], wherein the chronic renal failure is in the conservative stage; and

[7] a therapeutic method for treatment of chronic renal failure, which method uses the compound according to any one of [1] to [5] or a pharmaceutically acceptable salt thereof.

Effect of the Invention

By beginning administration of a compound represented by General Formula (1) or a pharmaceutically acceptable salt thereof (this may be hereinafter referred to as "compound of the present invention") after a renal disease progressed to cause chronic renal failure, not only suppression of decrease in the renal function to filtrate low-molecular substances, but also recovery of the function can be achieved. Further, since the compound of the present invention has effects to improve anemia which is a complication unique to chronic renal failure; as well as to increase the SOD activity, which decreases in chronic renal failure; and to suppresses decrease in OAT-3 involved in excretion of uremic substances; the compound of the present invention can ameliorate cardiovascular disturbances and vascular endothelial cell dysfunction due to chronic renal failure.

BEST MODE FOR CARRYING OUT THE INVENTION

Figure 1:
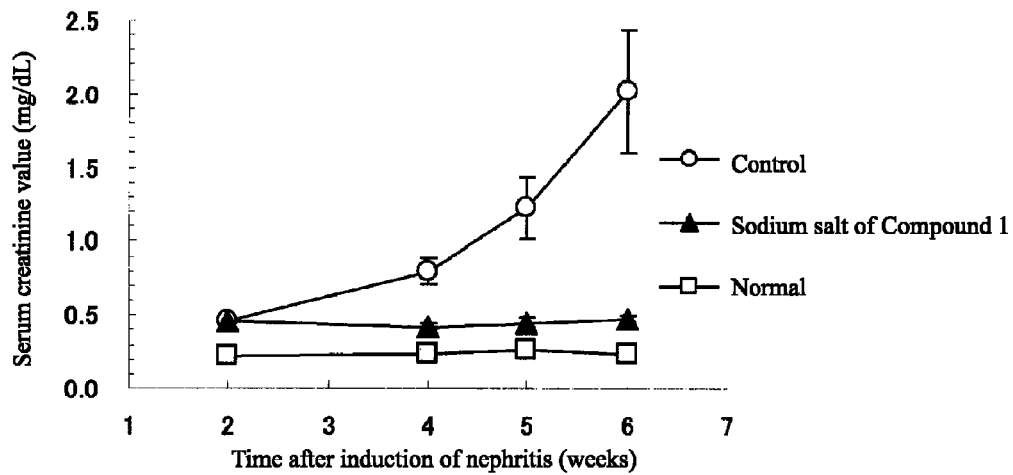
FIG. 1 shows serum creatinine values in a group of rats suffering from chronic renal failure to which the sodium salt of Compound 1 was administered.

Examples of the "aryl" in the compound represented by General Formula (1) include phenyl, 1-naphthyl and 2-naphthyl.

Examples of the "$C_1$-$C_6$ alkyl" include methyl, ethyl, n-propyl, isopropyl, n-butyl, isobutyl, sec-butyl, tert-butyl, n-pentyl, isopentyl, n-hexyl and isohexyl.

Examples of the "$C_2$-$C_6$ alkenyl" include vinyl, 1-propenyl, 2-propenyl, 1-butenyl, 2-butenyl, 3-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

Examples of the "$C_3$-$C_6$ cycloalkyl" include cyclopropyl, cyclobutyl, cyclopentyl and cyclohexyl.

Examples of the "$C_2$-$C_6$ alkylene" include ethylene, 1-methylethylene, 2-methylethylene, propylene, butylene, pentylene and hexylene.

Examples of the "$C_2$-$C_6$ alkenylene" include ethenylene, 1-propenylene, 2-propenylene, 1-butenylene, 2-butenylene, 3-butenylene, 1-pentenylene, 2-pentenylene, 3-pentenylene, 4-pentenylene, 4-methyl-3-pentenylene, 1-hexenylene, 2-hexenylene, 3-hexenylene, 4-hexenylene and 5-hexenylene.

Examples of the "$C_1$-$C_6$ alkoxy" in the "$C_1$-$C_6$ alkoxycarbonyl" include methoxy, ethoxy, n-propoxy, isopropoxy, n-butoxy, isobutoxy, sec-butoxy, tert-butoxy, n-pentyloxy, isopentyloxy, n-hexyloxy and isohexyloxy.

Examples of the "pharmaceutically acceptable salt" of the compound of the present invention include, in cases where the compound represented by General Formula (1) is basic, salts of inorganic acids such as hydrochloric acid, sulfuric acid, nitric acid, phosphoric acid, hydrofluoric acid and hydrobromic acid; and salts of organic acids such as acetic acid, tartaric acid, lactic acid, citric acid, fumaric acid, maleic acid, succinic acid, methanesulfonic acid, naphthalenesulfonic acid and camphorsulfonic acid.

Examples of the "pharmaceutically acceptable salt" of the compound of the present invention include, in cases where the compound represented by General Formula (1) is acidic, alkaline metal salts such as the sodium salt and the potassium salt; and alkaline earth metal salts such as the calcium salt.

Among the compounds represented by General Formula (1), Compound 1, wherein $R^1$ and $R^2$ represent phenyl; A represents $NR^5$; $R^5$ represents isopropyl; D represents butylene; G represents O; $R^3$ and $R^4$ represent hydrogen; and Q represents carboxyl; or a pharmaceutically acceptable salt thereof is most suitably used.

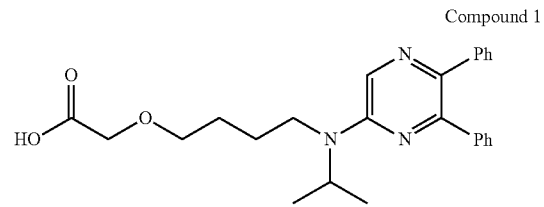

Compound 1

Further, among the compounds described above, compounds wherein carboxyl corresponding to Q in General Formula (1) is replaced with its equivalent $C_1$-$C_6$ alkoxycarbonyl (e.g., methoxycarbonyl), tetrazolyl or General Formula (2) are also especially suitably used. In particular, General Formula (2) wherein $R^6$ represents $C_1$-$C_6$ alkyl is preferred, and Compound 2, wherein $R^6$ represents $C_1$ alkyl (methyl), is especially preferably used.

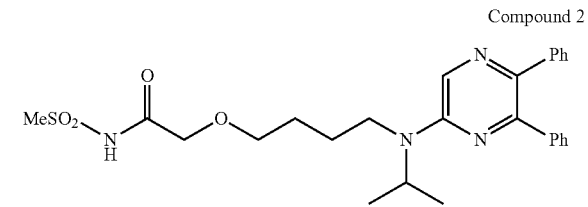

Compound 2

"Chronic renal failure" in the present invention means a state wherein renal filtration function gradually decreases for a long period of time and the functional abnormality persists over a long time. More particularly, it can be said to be a condition or a syndrome wherein blood urea nitrogen (BUN) and the serum creatinine value are high or increase persistently. This definition is essentially equivalent to the definitions in the textbooks described in the BACKGROUND ART section. More concretely, in the case of human, patients who show a serum creatinine value of not less than 1.4 mg/dL based on measurement by the enzyme method, which value is observed for not less than 1 month, can be securely diagnosed with chronic renal failure. In other animal species, the absolute value of serum creatinine may vary, but those can be diagnosed as having developed chronic renal failure when the value is higher than the normal range.

"Chronic renal failure in the conservative stage" in the present invention means, in chronic renal failure, the stage before end-stage chronic renal failure wherein maintenance of life is impossible without dialysis or renal transplantation. The present invention can be especially effectively employed for chronic renal failure in the conservative stage, in which most of the renal functions are decreased but still remain.

Further, the present invention can be especially effectively employed in cases where creatinine clearance, eGFR, or glomerular filtration rate (GFR) actually measured by the inulin clearance method or the like is less than 60 mL/min./1.73 $m^2$ in human, or in cases where these indices decreased to not more than 50% with respect to the normal values in animals. The present invention can be preferably employed also in cases where, in human, renal function decreased to less than 40 mL/min./1.73 $m^2$ or less than 30 mL/min./1.73 $m^2$.

Examples of the causative disease of chronic renal failure in the present invention include all the nephropathic diseases such as primary renal diseases; renal disorders due to systemic diseases; congenital renal diseases; renal infections; renal disorders due to nephrotoxic substances; and obstructive diseases of the urinary tract. Particular examples thereof include, but are not limited to, chronic glomerulonephritis; diabetic nephropathy; chronic pyelonephritis; acute progressive nephritis; gestosis; cystic kidney; nephrosclerosis; malignant hypertension; renal disorders due to various collagen diseases such as SLE; amyloid kidney; gouty kidney; metabolic disorder renal failure; tuberculosis; nephrolithiasis; kidney/urinary tract malignant tumors; obstructive uropathy; myeloma; and renal hypoplasia.

The renal failure whose treatment (this may be represented as "therapy") is possible by the present invention is chronic renal failure, especially chronic renal failure in the conservative stage. The present invention has an effect not only to improve decreased filtration function of the kidney, but also to improve cardiovascular disturbances and endothelial cell dysfunction which are especially problematic in chronic renal failure, by improving anemia and increasing the SOD activity.

"Anemia" in the present invention means anemia which occurs with chronic renal failure. More particularly, anemia can be diagnosed by a decreased erythrocyte count, hematocrit and/or hemoglobin content, and/or the like, and it is known that its incidence increases as the stage progresses after the renal function disorder stage.

Since, by the present invention, prophylaxis or therapy of anemia due to chronic renal failure is possible, clinical symptoms such as hypobulia, easy fatigability, breathlessness, postural vertigo and palpitation can be ameliorated. Further, since the therapeutic agent of the present invention can be orally administered, pain caused by subcutaneous injection can be avoided, and the agent can be easily taken every day at home without visiting a hospital, so that anemia can be securely ameliorated and various symptoms due to anemia can be controlled.

The ameliorating effect by the present invention on decrease in the SOD activity which is observed in chronic renal failure was revealed for the first time. Since SOD plays a central role in reduction/removal of oxidative stress in the living body, amelioration of further decrease in renal function due to increased oxidative stress can be expected in the present invention. Further, amelioration of cardiovascular events such as vascular dysfunction and vascular endothelial cell dysfunction, which are known to increase due to chronic renal failure, by the present invention can be expected.

In the present invention, it was revealed that the compound of the present invention suppresses decrease in OAT-3, an organic anion transporter in a major excretion pathway for indoxyl sulphate which is important as a uremic substance. Therefore, it is expected that administration of the compound of the present invention may suppress decrease in excretion of indoxyl sulphate. Further, in cases where anion transporters are involved in excretion of an agent, side effects of the agent can be reduced by suppression of increase in its blood level, and an appropriate dose of the agent can be easily determined.

Thus, since the compound of the present invention shows the effects of amelioration of anemia, increase in renal SOD and suppression of decrease in drug transporters in chronic renal failure, the compound of the present invention has extremely preferable traits as an agent to be used for chronic renal failure.

The compound of the present invention can be produced by a known method, for example, the one described in WO 2002/088084.

Further, in the present invention, the therapeutic agent may contain not less than two kinds of compounds of the present invention, or may contain another prostaglandin $I_2$ derivative as mentioned above and/or a known therapeutic agent for a renal disease. Examples of such an agent include angiotensin converting enzyme inhibitors and angiotensin II receptor blockers, as well as antihypertensive drugs such as calcium blockers and β blockers. Further, the therapeutic agent of the present invention may be preferably used in combination with an antiplatelet drug such as persantin or dipyridamole; a statin whose therapeutic effect has been reported for renal diseases; and/or the like, or may be prepared as a mixture therewith.

Further, since the compound of the present invention can be used for treatment of anemia due to chronic renal failure, it is also possible to use it in combination with a rHuEPO preparation and/or an iron preparation, thereby enabling to increase the dosing interval and to reduce the side effects of the rHuEPO preparation and/or the iron preparation. Further, preparation of a mixture with such preparations; and usage with another SOD preparation and/or oxidative stress inhibitor, and preparation of a mixture therewith; are also possible.

The present invention can be used effectively especially in mammals. It can be used in human, and can also be used for therapy of non-human mammals, preferably pet animals such as dog, cat, rabbit, rat and guinea pig. Further, the present invention can be used as a therapeutic method for treatment of chronic renal failure.

In cases where the therapeutic agent of the present invention for chronic renal failure is used in human, the suitable dose is 1 to 10000 μg/adult, preferably 5 to 5000 μg/adult per administration in terms of the amount of the compound represented by Formula (1) as an active ingredient, which is administered 1 to 4 times per day for 1 day or longer, preferably for not less than 3 days.

In cases where the therapeutic agent of the present invention is used in a non-human mammal, the suitable dose is 0.1 μg/kg to 100 mg/kg, preferably 1 μg/kg to 50 mg/kg in terms of the amount of the compound represented by Formula (1) as an active ingredient, which is administered 1 to 4 times per day for 1 day or longer, preferably for not less than 3 days.

The administration method may be any administration method, and examples thereof include, but are not limited to, oral administration, subcutaneous administration, intravenous and intravascular administration, intramuscular administration, pulmonary administration, intraduodenal administration and intraperitoneal administration. Further, a method wherein the drug is directly administered to a damaged area in a tissue or organ showing an especially remarkable damage, which administration is carried out in a direct manner or after being impregnated in an appropriate base, is also preferably used.

In cases where the therapeutic agent of the present invention for chronic renal failure contains a known therapeutic agent for chronic renal failure as an additional component, the above-described dose may be reduced in consideration of the action and effect of the additional component.

As the therapeutic agent of the present invention for chronic renal failure, one or several kinds of derivatives may be used as they are, or these may be orally administered in the form of a solid containing the additives described below. Examples of the additives include excipients such as starches, lactose, sucrose, glucose, mannitol, calcium carbonate and calcium sulfate; binders such as starches, dextrin, gum arabic, gum tragacanth, methyl cellulose, gelatin, polyvinyl pyrrolidone and polyvinyl alcohol; disintegrating agents such as starches, polyvinyl pyrrolidone and crystalline cellulose; lubricants such as magnesium stearate and talc; coloring agents; and flavoring agents.

The therapeutic agent of the present invention for chronic renal failure can be used in various dosage forms, and particular examples thereof include dosage forms which are conventionally used, such as tablets, sugar-coated tablets, powders, granules, troches, capsules, balls, syrups and sprays. Further, the therapeutic agent of the present invention may be parenterally administered in the form of a sterilized solution, and another solute, such as sodium chloride or glucose necessary to make the agent solution isotonic, may also be used.

Depending on the characteristics of the respective drugs, release controls such as those attaining sustained release or delayed release may be applied. In such cases, a wide variety administration methods may be employed for both oral and parenteral administration, and examples thereof include a method using an implantable pump for sustained-releasing (for example, Alzet minipump) and a method using the drug dispersed in a biodegradable polymer which is gradually degraded in the intestinal tract.

EXAMPLES

The present invention will now be described in more detail by way of Examples below, but the present invention is not restricted to these Examples.

Example 1

Platelet Aggregation Inhibition Action in Rat
(Experimental Method)

To determine the dose with which the $PGI_2$-receptor agonistic activity is equivalent between the sodium salt of Compound 1 and beraprost sodium, the platelet aggregation inhibition action which is the major pharmacological action of $PGI_2$-receptor agonists was used as an index for comparison. The sodium salt of Compound 1 (30 mg/kg) or beraprost sodium (0.3 mg/kg) was orally administered to rats fasted for 1 day, and blood was collected therefrom at the time when the plasma level of each compound became maximum, that is, 1 hour after the administration of the sodium salt of Compound 1 (Non-patent Document: J Pharmacol Exp Ther 322:1181-1188 2007) or 0.5 hour after the administration of beraprost sodium (Non-patent Document: Xenobiotic Metabolism and Disposition 6:713-725 1989), followed by measuring ADP-induced rat platelet aggregation. In the both groups, the experiment was carried out with n=6. The sodium salt of Compound 1, which was one of the $PGI_2$-receptor agonists used herein, was synthesized by treating a carboxylic acid with sodium hydroxide, which carboxylic acid was synthesized according to the method described in Patent Document 4.

(Results)

The rate of suppression of rat platelet aggregation upon stimulation with 10 µM ADP was 47.0±7.9% in the group to which the sodium salt of Compound 1 was administered, and 64.2±8.3% in the group to which beraprost sodium was administered, showing that beraprost sodium has a stronger tendency of suppression, but there was no statistical difference between these (t test). As a result, it was revealed that the sodium salt of Compound 1 at a dose of 30 mg/kg shows an almost equivalent $PGI_2$-receptor agonistic activity with beraprost sodium at a dose of 0.3 mg/kg.

Example 2

Pharmacological Effect in Rats Suffering from Chronic Renal Failure
(Experimental Method)

Rabbit anti-rat glomerular basement membrane antiserum (14-fold diluted, 3 mL/kg) was intravenously injected to WKY rats of 8 weeks old, to induce glomerulonephritis. Two weeks after the induction of nephritis, blood was collected, and it was confirmed that the serum creatinine value has been significantly increased at this time and hence that chronic renal failure has already occurred (normal group: 0.23±0.01 mg/dL, N=4; nephritis-induced group: 0.47±0.01 mg/dL, N=21; t test). Further, creatinine clearance, which is used as an alternative to glomerular filtration rate (GFR), was 2.63±0.07 mL/min. (N=3) in the normal group, and 1.22±0.04 mL/min. (N=21) in the nephritis-induced group. That is, creatinine clearance in the nephritis-induced group decreased to not more than 50% with respect to that of the normal group, and therefore it was confirmed that the nephritis-induced group developed chronic renal failure whose primary disease was glomerulonephritis. Thus, the time of establishment of the chronic renal failure was defined as 2 weeks after the induction of nephritis. Six weeks after the induction of nephritis, creatinine clearance was 0.33±0.10 mL/min. in the control group, which corresponded to 10.2% of that of the normal group (3.24±0.13 mL/min.). This stage was the phase in which introduction of dialysis is considered in human, and corresponded to the most serious phase in chronic renal failure in the conservative stage.

Thus, 2 weeks after the induction of nephritis, based on the serum creatinine value, the rats suffering from chronic renal failure were grouped into the normal group (with neither induction of nephritis nor administration, n=4), the control group (administration of only a vehicle, n=7), the group to be treated with the sodium salt of Compound 1 (administration of 30 mg/kg twice a day, n=7) and the group to be treated with beraprost sodium (administration of 0.3 mg/kg twice a day, n=7), after which oral administration of the drugs were begun, followed by daily administration thereof. As the vehicle for the drugs, 0.25% sodium carboxymethylcellulose solution was used.

From 2 weeks after the induction of nephritis when the chronic renal failure was established, until 6 weeks after the induction of nephritis, urine collection and blood collection were carried out as appropriate, and the serum creatinine value, BUN and creatinine clearance were measured for each group to evaluate renal function. Further, the hematocrit, the hemoglobin content, and the SOD activity of the renal tissue, which are closely linked to the diseased state of chronic renal failure, were measured, and the expression level of mRNA of an organic anion transporter OAT-3 was quantified. The SOD activity was measured with the SOD assay kit WST (Dojindo Laboratories), and the expression level of mRNA of OAT-3 was quantified using LightCycler FastStart DNA Master SYBR Green I (Roche).

Six weeks after the induction of nephritis when the chronic renal failure in the conservative stage progressed to a serious phase in the control group, a statistical analysis was carried out. In terms of statistical difference, homoscedasticity was tested by the Bartlett's test between the control group and the respective drug-administered groups. In homoscedastic cases, the parametric Dunnett's test was carried out between the respective drug-administered groups and the control group, while in heteroscedastic cases, the nonparametric Dunnett's test was carried out therebetween, using a significance level of less than 5%.

(Result 1)

Figure 2:
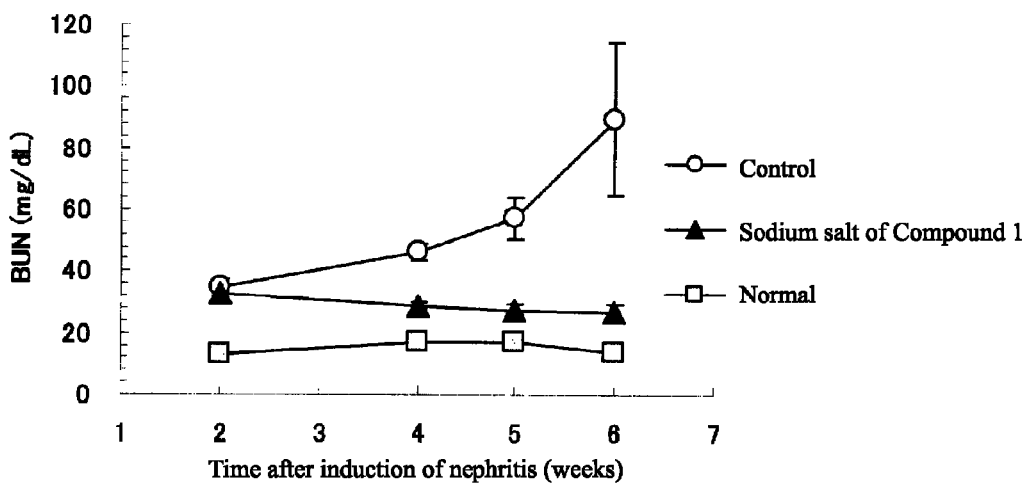
FIG. 2 shows BUN in a group of rats suffering from chronic renal failure to which the sodium salt of Compound 1 was administered.
Figure 3:
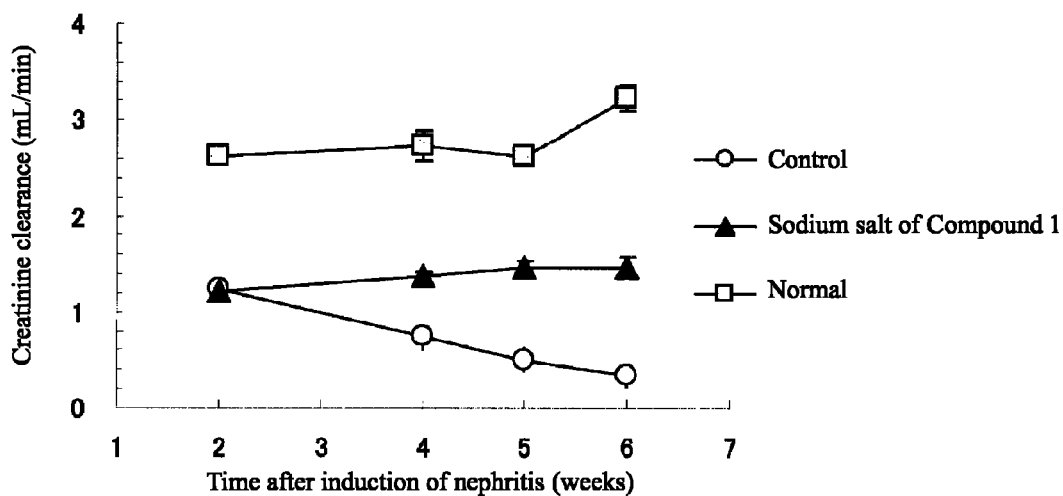
FIG. 3 shows creatinine clearance in a group of rats suffering from chronic renal failure to which the sodium salt of Compound 1 was administered.

As shown in FIG. 1, the serum creatinine value in the group to which the sodium salt of Compound 1 was administered kept low compared to that in the control group until 6 weeks after the induction of nephritis. As shown in FIG. 2, BUN in the group to which the sodium salt of Compound 1 was administered kept low compared to that in the control group until 6 weeks after the induction of nephritis. As shown in FIG. 3, creatinine clearance in the group to which the sodium salt of Compound 1 was administered kept high compared to that in the control group until 6 weeks after the induction of nephritis. Further, creatinine clearance in the group to which the sodium salt of Compound 1 was administered was significantly increased 6 weeks after the induction of nephritis relative to that at the beginning of the administration (2 weeks after the induction of nephritis) (2 weeks after the induction: 1.21±0.06 mL/min.; 6 weeks after the induction: 1.48±0.11 mL/min.; t-test), so that it was shown that the sodium salt of Compound 1 has not only an effect to suppress progression of the diseased state of chronic renal failure but also an evident effect to ameliorate the renal filtration function.

The results of comparison of the actions of the respective drugs 6 weeks after the induction of nephritis are shown in Table 1. The serum creatinine value in the group to which the sodium salt of Compound 1 was administered was significantly lower than that of the control group, but no statistical difference in the serum creatinine value was found between the group to which beraprost sodium was administered and the control group (nonparametric Dunnett's test). BUN in the group to which the sodium salt of Compound 1 was administered was significantly lower than that of the control group, but no statistical difference in BUN was found between the group to which beraprost sodium was administered and the control group (nonparametric Dunnett's test). Creatinine clearance in the group to which the sodium salt of Compound 1 was administered was significantly higher than that of the control group, and creatinine clearance in the group to which beraprost sodium was administered was also significantly higher than that of the control group (parametric Dunnett's test).

From the results above, it was shown that the sodium salt of Compound 1 has a more excellent ameliorating effect on renal function compared to beraprost sodium.

TABLE 1

Parameters of renal function in rats suffering from chronic renal failure, 6 weeks after induction of nephritis

| | Serum creatinine value (mg/dL) | BUN (mg/dL) | Creatinine clearance (mL/min.) |
|---|---|---|---|
| Control | 2.03 ± 0.42 | 89.6 ± 25.1 | 0.33 ± 0.10 |
| Sodium salt of Compound 1 | 0.47 ± 0.04* | 26.8 ± 2.49* | 1.48 ± 0.11* |
| Beraprost sodium | 0.85 ± 0.12 | 42.1 ± 6.41 | 0.77 ± 0.13* |

Each value in the table indicates mean ± standard error calculated from 7 cases in each group. The serum creatinine value, BUN and creatinine clearance in the normal group (4 cases) were 0.24 ± 0.01 mg/dL, 13.5 ± 0.09 mg/dL and 3.24 ± 0.13 mL/min., respectively. The serum creatinine value and BUN were subjected to the nonparametric Dunnett's test, and creatinine clearance was subjected to the parametric Dunnett's test.
p: *<0.05, based on comparison with the control group.

(Result 2)

By 6 weeks after the induction of nephritis, the hematocrit (32.0±2.09%) and the hemoglobin content (11.8±0.69 g/dL) in the control group significantly decreased compared to those in the normal group (with a hematocrit of 44.1±0.34% and a hemoglobin content of 16.0±0.09 g/dL) (t test, p<0.05). Since the values in the control group were almost the same as those in other rats suffering from glomerulonephritis (Non-patent Document: Mol Med 4:413-424 1998) and ICGN mice which spontaneously develop renal anemia (Non-patent Document: J Vet Med Sci 66:423-431 2004), the present chronic renal failure rats were also considered to have developed renal anemia. As shown in Table 2, the hematocrit and the hemoglobin content in the group to which the sodium salt of Compound 1 was administered were significantly higher than those in the control group. Although the hematocrit and the hemoglobin content in the group to which beraprost sodium was administered were higher than those in the control group, they did not show statistical difference therebetween (nonparametric Dunnett's test). Thus, it was suggested that the sodium salt of Compound 1 has an ameliorating effect on anemia.

TABLE 2

Hematocrit values and hemoglobin contents in rats suffering from chronic renal failure, 6 weeks after induction of nephritis

| Group | Hematocrit value (%) | Hemoglobin content (g/dL) |
|---|---|---|
| Control | 32.0 ± 2.09 | 11.8 ± 0.69 |
| Sodium salt of Compound 1 | 37.1 ± 0.71* | 13.7 ± 0.28* |
| Beraprost sodium | 33.9 ± 0.97 | 12.3 ± 0.28 |

Each value in the table indicates mean ± standard error calculated from 7 cases in each group. The hematocrit value and the hemoglobin content in the normal group (4 cases) were 44.1 ± 0.34% and 16.0 ± 0.09 g/dL, respectively. The nonparametric Dunnett's test was carried out.
*p < 0.05, based on comparison with the control group.

(Result 3)

The results of measurement of the SOD activity in the renal tissue 6 weeks after the induction of nephritis are shown in Table 3. The SOD activity in the group to which the sodium salt of Compound 1 was administered was significantly higher than that of the control group. Although the SOD activity in the group to which beraprost sodium was administered was higher than that in the control group, it did not show statistical difference therebetween (parametric Dunnett's test). Thus, it was suggested that the sodium salt of Compound 1 has an effect to ameliorate oxidative stress due to increase in the SOD activity.

TABLE 3

The SOD activity in the renal tissue of rats suffering from chronic renal failure, 6 weeks after induction of nephritis

| Group | SOD activity (%, taking the activity in the normal group as 100%) |
|---|---|
| Control | 63.1 ± 5.68 |
| Sodium salt of Compound 1 | 83.6 ± 2.52* |
| Beraprost sodium | 67.9 ± 5.45 |

Each value in the table indicates mean ± standard error calculated from 7 cases in each group. The calculation was carried out taking the SOD activity in the normal group (4 cases) as 100%. The parametric Dunnett's test was carried out.
*p < 0.05, based on comparison with the control group.

(Result 4)

The results of quantification of mRNA of the organic anion transporter OAT-3 expressed in the renal cortex 6 weeks after the induction of nephritis are shown in Table 4. The expression level of OAT-3 in the group to which the sodium salt of Compound 1 was administered was significantly higher than that of the control group. Although the expression level of OAT-3 in the group to which beraprost sodium was administered was higher than that in the control group, it did not show statistical difference therebetween (parametric Dunnett's test). Thus, it was suggested that the sodium salt of Compound 1 has an effect to ameliorate excretion of uremic substances by suppressing decrease in the transporter OAT-3.

TABLE 4

The expression level of mRNA of OAT-3 in the renal cortex of rats suffering from chronic renal failure, 6 weeks after induction of nephritis

| Group | Expression level of mRNA of OAT-3 (ratio to that of GAPD) |
|---|---|
| Control | 0.15 ± 0.03 |
| Sodium salt of Compound 1 | 0.42 ± 0.05* |
| Beraprost sodium | 0.24 ± 0.04 |

Each value in the table indicates mean ± standard error calculated from 7 cases in each group.
The expression level of mRNA of OAT-3 in the normal group (4 cases) was 1.00 ± 0.06.
*The parametric Dunnett's test was carried out: $p < 0.05$, based on comparison with the control group.

Example 3

Figure 4:
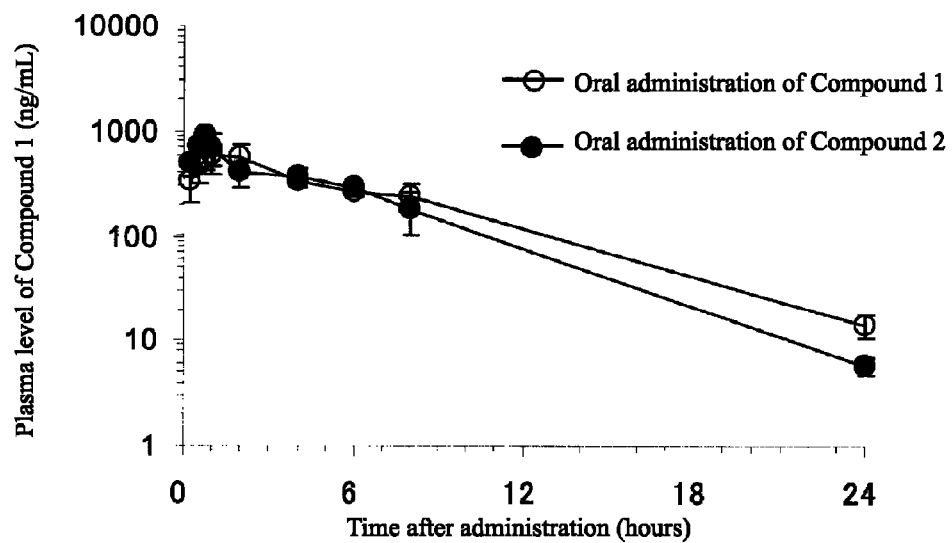
FIG. 4 shows changes in the plasma level of Compound 1 after oral administration of Compound 1 and Compound 2.

Changes in Plasma Level of Compound 1 with Time after Administration of Compound 1 and Compound 2 to Rats Compound 1 or Compound 2 was orally administered to rats in an amount of 5 mg/kg, and Compound 1 was intravenously administered in an amount of 1 mg/kg, after which the concentration of Compound 1 in plasma was measured. The experiment was carried out with n=3 in each of the both groups. Compound 2 was converted to Compound 1 in the living body, and the bioavailability was not statistically different from that in the case of direct administration of Compound 1 (Table 5), showing overlapping changes in the plasma level of Compound 1 between these cases as shown in FIG. 4. Thus, it was shown that Compound 2 can be used in a manner similar to Compound 1. Compound 1 and Compound 2 used in this experiment was synthesized in accordance with the method described in Patent Document 4.

TABLE 5

Bioavailability observed upon administration of Compound 1 and Compound 2 to rats

| | Compound 1 | Compound 2 |
|---|---|---|
| Bioavailability (%)[1] | 43.3 ± 2.6 | 47.1 ± 7.0 |

[1] Value after correction for the molecular weight.
Mean ± standard error calculated from 3 cases in each group.

As described above, the sodium salt of Compound 1 and beraprost sodium were orally administered to rats suffering from chronic renal failure in amounts equivalent to each other in terms of the $PGI_2$-receptor agonistic activity, to study their therapeutic effects on chronic renal failure. As a result, it was revealed that the sodium salt of Compound 1 has effects superior to beraprost sodium in terms of amelioration of renal function, amelioration of anemia, amelioration of the SOD activity and amelioration of decrease in OAT-3, which is involved in excretion of uremic substances. Therefore, the compound of the present invention represented by the sodium salt of Compound 1 was shown to be extremely useful as a therapeutic agent for chronic renal failure compared to the other known compounds.

The invention claimed is:

1. A method for the treatment of chronic renal failure, which comprises administering to a patient in need thereof an effective amount of a compound represented by General Formula (1) below:

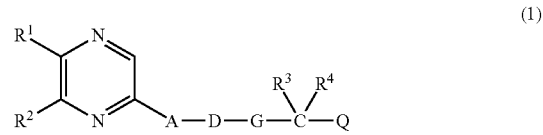

(1)

wherein
  $R^1$ and $R^2$ each independently represents aryl;
  A represents $NR^5$, O, S, SO or $SO_2$;
  $R^5$ represents $C_1$-$C_6$ alkyl, $C_2$-$C_6$ alkenyl or $C_3$-$C_6$ cycloalkyl;
  D represents $C_2$-$C_6$ alkylene or alkenylene;
  G represents O, S, SO or $SO_2$;
  $R^3$ and $R^4$ each independently represents hydrogen or $C_1$-$C_6$ alkyl; and
  Q represents carboxyl, $C_1$-$C_6$ alkoxycarbonyl, tetrazolyl or General Formula (2) below:

$$—CONH—SO_2—R^6 \quad (2)$$

wherein $R^6$ represents $C_1$-$C_6$ alkyl;
or a pharmaceutically acceptable salt thereof.

2. The method for the treatment of chronic renal failure according to claim 1, wherein:
  $R^1$ and $R^2$ represent phenyl;
  $R^5$ represents $C_1$-$C_6$ alkyl;
  D represents $C_2$-$C_6$ alkylene;
  G represents O;
  $R^3$ and $R^4$ represent hydrogen; and
  Q represents carboxyl or General Formula (2).

3. The method for the treatment of chronic renal failure according to claim 1 or 2, wherein:
  A represents $NR^5$;
  $R^5$ represents $C_3$-$C_6$ branched alkyl;
  D represents butylene; and
  Q represents carboxyl or General Formula (2).

4. The method for the treatment of chronic renal failure according to claim 1, wherein:
  $R^5$ represents isopropyl; and
  Q represents carboxyl or General Formula (2).

5. The method for the treatment of chronic renal failure according to claim 1, wherein:
  Q represents carboxyl.

6. The method for the treatment of chronic renal failure according to claim 1, wherein said chronic renal failure is in the conservative stage.

* * * * *

UNITED STATES PATENT AND TRADEMARK OFFICE
CERTIFICATE OF CORRECTION

| | | |
|---|---|---|
| PATENT NO. | : 8,575,175 B2 | Page 1 of 1 |
| APPLICATION NO. | : 13/055242 | |
| DATED | : November 5, 2013 | |
| INVENTOR(S) | : Matsuda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this
Eighteenth Day of August, 2015

Michelle K. Lee
*Director of the United States Patent and Trademark Office*